United States Patent [19]
Falciani et al.

[11] 4,354,023
[45] Oct. 12, 1982

[54] CEFADROXIL ACETYLCYSTEINATE SALT

[75] Inventors: Marco Falciani; Renato Broggi, both of Milan, Italy

[73] Assignee: Dobfar S.p.A., Milan, Italy

[21] Appl. No.: 240,310

[22] Filed: Mar. 4, 1981

[51] Int. Cl.³ .......................................... C07D 501/22
[52] U.S. Cl. .................................. 544/030; 424/246
[58] Field of Search ...................... 544/16, 30, 28, 22; 424/246

[56]          References Cited
         U.S. PATENT DOCUMENTS 3,984,403  10/1916  Fujisawa et al. ...................... 544/30
3,985,741  10/1976  Crast et al. ........................... 424/246

Primary Examiner—Nicholas S. Rizzo
Attorney, Agent, or Firm—Oblon, Fisher, Spivak, McClelland & Maier

[57]              ABSTRACT

Salts of cefadroxil with an amino acid selected from the group consisting of L-lysine, L-arginine and acetylcysteine. Said salts are obtained by reacting an aqueous suspension of cefadroxil with an aqueous solution of an amino acid or its derivative, selected from the group consisting of L-lysine, L-arginine and acetylcysteine. To isolate the salt, the aqueous solution is submitted to lyophilization.

1 Claim, No Drawings

CEFADROXIL ACETYLCYSTEINATE SALT

BACKGROUND OF THE INVENTION

1. Field of the Invention

The present invention relates to novel cefadroxil salts with amino acids, said salts having antibiotic activity.

2. Description of the Prior Art

Cefadroxil is a well known antibiotic, which is described in U.S. Pat. No. 3,985,741.

It is usually administered orally.

DETAILED DESCRIPTION OF THE INVENTION

It is an object of the present invention to provide new salts of cefadroxil which are injectable without inducing painful reactions when administered.

It is another object of the present invention to provide new salts of cefadroxil which increase the absorption of the antibiotic substance and which, when absorbed, are able to give and to join with the antibiotic activity which is peculiar to cefadroxil, their own specific activity which may have same interest from the pharmacological point of view.

Said and other objects are attained by means of the salification of cefadroxil with an amino acid selected from the group consisting of L-lysine, L-arginine and acetylcysteine.

To obtain this salification cefadroxil is reacted in aqueous suspension and at room temperature with an aqueous solution of an amino acid or its derivative, selected from the group consisting of L-lysine, L-arginine or acetylcysteine, the salt being isolated from the aqueous solution by means of lyophilization.

In order that this invention may be readily available to and understood by those skilled in the art, methods of preparing each of the three salts, which are object of the present invention, are described in the following example, which are given merely in illustration of the present invention.

EXAMPLE 1

Cefadroxil arginine salt having formula:

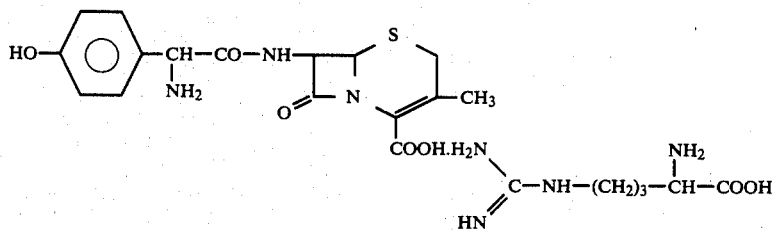

To a suspension of cefadroxil dimethylformamide solvate (43.6 g, 0.1 mole) in distilled water (300 ml) was added L-arginine (21 g, 0.1 mole); pH raised up to 8 and complete dissolution was obtained.

3 g of decolorizing carbon were added to the resultant solution, which was filtered through a material commercially known as decalite. The resultant solution was poured into a tray, till a 1 cm layer was obtained; after pre-freezing, the solution was freezed at −40° C. and lyophilization was started. Lyophilization was finished in 36 hours.

After lyophilization the product was screened and 50.1 g of arginine salt of cefadroxil were obtained.

KF 1%.

TLC Single product.

Eluant acetonitrile:water:formic acid=20:5:2 $[\alpha]_D$ (C=1, H$_2$O)+118°.

Microbiological titer: 665 mcg/mg as cefadroxil dry base. Same result was obtained employing cefadroxil monohydrate (38.1 g) instead of cefadroxil dimethylformamide solvate.

EXAMPLE 2

Cefadroxil acetylcysteinate having formula:

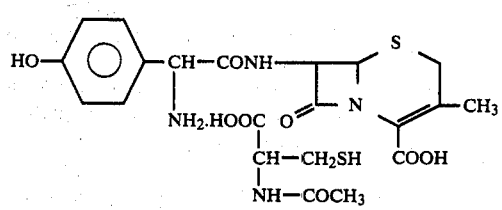

To a suspension of cefadroxil dimethylformamide solvate (43.6 g, 0.1 mole) in distilled water (350 ml) was added N-acetylcysteine (16.32 g, 0.1 mole), dissolved in distilled water (200 ml), at 15°–20° C.

Complete dissolution was obtained; carbon (2.5 g) was added after 30 minutes to the resultant solution at 0° C. After 30 minutes stirring, the solution was filtered through a material commercially known as decalite. The resultant clear solution was poured into a tray, till a 1 cm layer was obtained, was frozen at −40° C. and lyophilized. Lyophilization lasted 36 hours.

The obtained white crystalline product was screened and 49 g of cefadroxil acetylcysteinate were obtained.

KF 0.7%.

TLC single product.

Eluant acetonitrile:water:formic acid=20:5:2 $[\alpha]_D$ (c=1, H$_2$O)=+115°.

$E_1$ $_{cm}$1% at 262 nm=163.

Microbiological titer: 668 mcg/mg as cefadroxil dry base. Same result was obtained employing cefadroxil monohydrate (38.1 g) instead of cefadroxil dimethylformamide solvate.

EXAMPLE 3

Cefadroxil lysinate having formula:

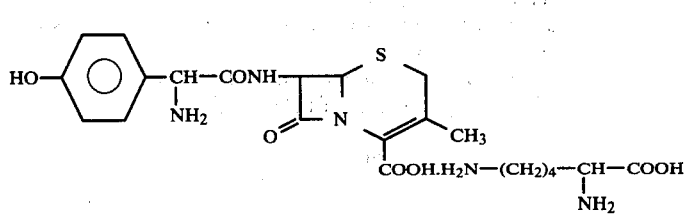

Bidistilled water (600 ml) and cefadroxil dimethylformamide solvate (43.6 g, 0.1 mole) were charged at 0° C. in a reaction vessel. A 50% L-lysine base aqueous solution, containing 14.6 g (0.1 mole), was added to the resultant suspension; the mixture was kept under stirring for 1 hour at 0° C. A complete dissolution was obtained and the pH value raised up to 8.5; Decolorizing carbon (1.5 g) was added to the resultant solution, which was filtered through filter plates and poured into a tray, till a 1 cm layer was obtained.

The solution was then frozen at −35° C. and lyophilized. The resulting material was discharged and screened; cefadroxil lysinate (48 g) was obtained.

KF 1.3%.

TLC single product $[\alpha]_D$ (c=1, $H_2O$)= +110°.

Microbiological titer: 709 mcg/mg as cefadroxil dry base. Same result was obtained employing cefadroxil monohydrate (38.1 g) instead of cefadroxil dimethylformamide solvate.

What is claimed is:

1. Cefadroxil salt which is cefadroxil acetylcysteinate having formula:

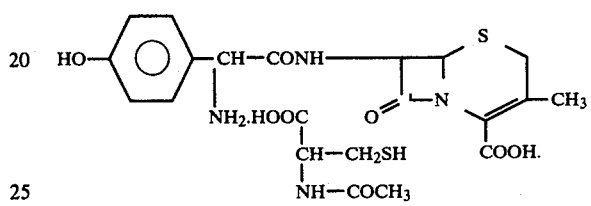

UNITED STATES PATENT AND TRADEMARK OFFICE
CERTIFICATE OF CORRECTION

PATENT NO. : 4,354,023

DATED : October 12, 1982

INVENTOR(S) : Marco Falciani et al

It is certified that error appears in the above-identified patent and that said Letters Patent is hereby corrected as shown below:

On the title page,

Please insert the following Foreign Application Priority Data:

[30] -- April 1, 1980  [IT] Italy .....21098 A --

Signed and Sealed this

Eighth Day of February 1983

[SEAL]

Attest:

GERALD J. MOSSINGHOFF

Attesting Officer        Commissioner of Patents and Trademarks